United States Patent

Tughan

Patent Number: 5,849,907
Date of Patent: Dec. 15, 1998

[54] CHEMICAL PROCESS

[75] Inventor: Garfield Cecil Tughan, Hertfordshire, Great Britain

[73] Assignee: Glaxo Wellcome SpA, Verona, Italy

[21] Appl. No.: 967,723

[22] Filed: Nov. 7, 1997

Related U.S. Application Data

[63] Continuation of Ser. No. 507,386, Aug. 31, 1995, abandoned.

[30] Foreign Application Priority Data

Mar. 20, 1993 [GB] United Kingdom ............... 9305853

[51] Int. Cl.⁶ .................................................. C07D 477/00
[52] U.S. Cl. ............................................... 540/302
[58] Field of Search ............................... 540/302

[56] References Cited

U.S. PATENT DOCUMENTS 4,181,733  1/1980  Christensen et al. .

FOREIGN PATENT DOCUMENTS

A-0 416 953  3/1991  European Pat. Off. .

*Primary Examiner*—Rebecca Cook
*Attorney, Agent, or Firm*—Bacon & Thomas, PLLC

[57] ABSTRACT

A process for the preparation of the antibacterial compound

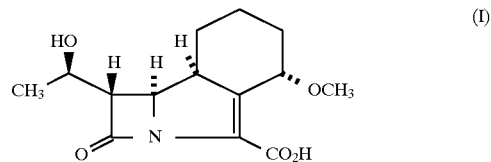

(I)

or a salt thereof which comprises hydrogenolysis of the novel compound of formula (II)

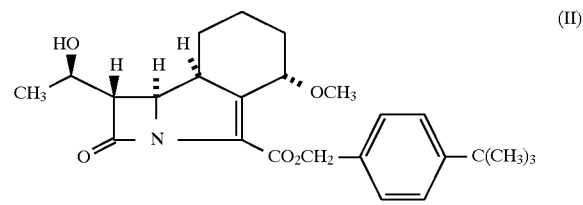

(II)

and if necessary or desired isolating the resultant carboxylic acid as a salt thereof.

8 Claims, No Drawings

CHEMICAL PROCESS

This application is a Continuation of application Ser. No. 08/507,386, filed Aug. 31, 1995, now abandoned, which is a 371 of PCT/EP94/00839, filed Mar. 17, 1994.

The present invention relates to an improved process for the synthesis of an antibacterial agent and to a novel intermediate for use in this process.

European Patent Application, publication No. 0416953A2 describes a novel class of tricyclic antibacterial agent and processes for their preparation. A particularly preferred compound described therein is (4S, 8S, 9R, 10S, 12R)-4-methoxy-10-(1-hydroxyethyl)-11-oxo-1 azatricyclo [7,2,0,0$^{3.8}$]undec-2-ene-carboxylic acid and physiologically acceptable salt thereof. Further the specification teaches that the compound may be prepared by the following process.

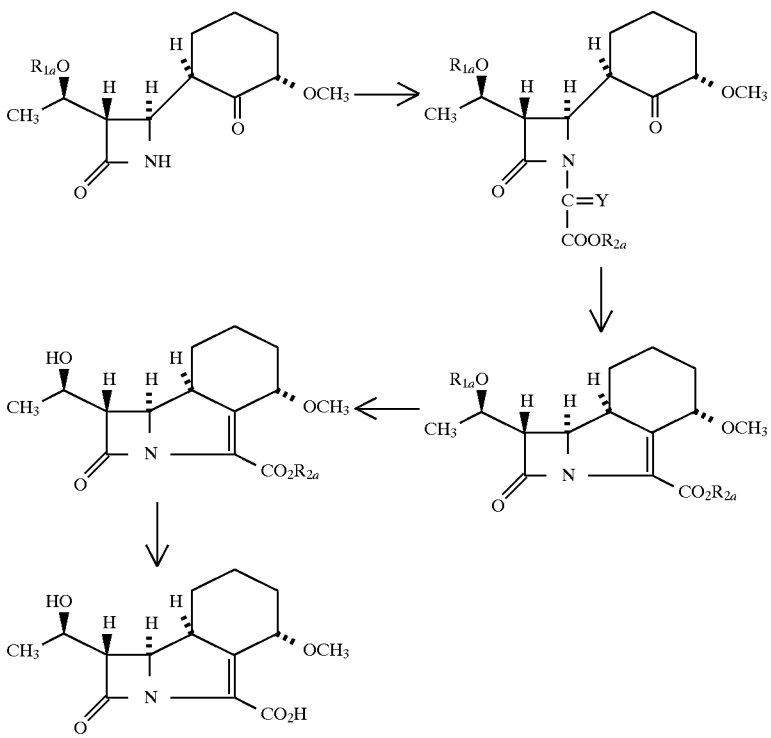

In the above formulae $R_{1a}$ represents a hydroxyl protecting group in particular t-butyldimethylsilyl, Y represents oxygen or a phosphine group, and $R_{2a}$ represents a carboxyl protecting group including arymethyl e.g. benzyl or allyl. More specifically the specification contains examples of the synthesis of the compound using intermediates wherein $R_{1a}$ represents a t-butyldimethylsilyl group, Y is oxygen and $R_{2a}$ is allyl or $R_{1a}$ represents t-butyldimethylsilyl, Y is $PPh_3$ and $R_{2a}$ is benzyl.

In these examples the various intermediates are obtained as oils and this is not particularly desirable in a multi-step synthesis for use as a manufacturing process. It has surprisingly been found that the suitability of processes described above for use on a plant scale can be significantly improved if the t-butylbenzyl group is used as the carboxyl protecting group in the above synthesis. In particular the final Intermediate shown here below.

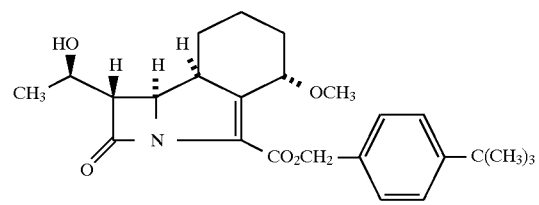

is a solid and its properties are such that it allows for a relatively simple purification step, for example recrystallisation, if desired before the final step in the synthesis is carried out.

Thus the present invention provides a process for the preparation of the compound of formula (I)

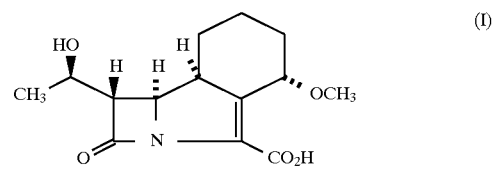

or a salt thereof which comprises hydrogenolysis of the compound of formula (II)

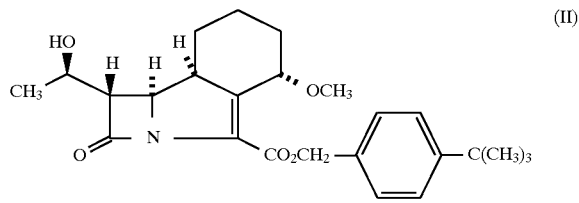

and if necessary or desired converting the resultant carboxylic acid into a salt thereof. The hydrogenolysis reaction is conveniently carried out using hydrogen and a metal catalyst such as palladium and in a solvent such as an alkanol e.g. ethanol, isopropanol, esters e.g. ethyl acetate or ketone e.g. acetone. This reaction is preferably caried out in the presence of a base, and suitable bases for use in the reaction include tertiary organic bases such as trialkylamines e.g. triethylamine. The carboxylic acid (I) or a salt thereof may conveniently be converted into a physiologically acceptable salt thereof without isolation of the product of the hydrogenolysis. Thus for example the sodium salt thereof may be obtained by the addition of acetone and sodium ethylhexanoate to the reaction solution, followed by addition of a non solvent such as an ether e.g. diisopropyl ether. In this process it may be advantageous to add seed crystals of the required sodium salt.

Salts of the compound of formula (I) include physiologically acceptable salts thereof and non physiologically acceptable salts thereof.

Suitable physiologically acceptable salts of compound of formula (I) include salts formed with alkali metals e.g. sodium or potassium, alkaline earth metals e.g. calcium, amino acids (e.g. lysine and arginine) and organic bases (e.g. procaine, phenylbenzylamine, ethanolamine, diethanolamine and N-methyl glucosamine). Non physiologically acceptable salts of the compound of formula (I) may be useful as intermediates for the preparation and/or isolation of the compound of formula (I) or a physiologically acceptable salt thereof.

The compound of formula (II) is novel and represents a further aspect of the invention.

The compound of formula (II) may be prepared by cyclisation of the compound of formula (III).

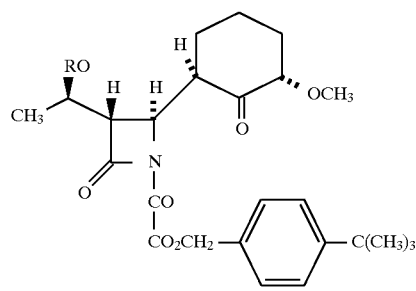

wherein R is a hydroxyl protecting group, followed by removal of the hydroxyl protecting group R.

Suitable hydroxyl protecting groups include those conventional hydroxyl protecting groups which may be removed by hydrolysis under buffered condition or non aqueous condition. Examples of such groups include hydrocarbyl silyl groups such a tri($C_{1-4}$alkyl)silyl group e.g. t-butyldimethylsilyl or trimethylsilyl.

The cyclisation reaction is carried by treating the compound of formula (III) with the phosphorus compound (IV)

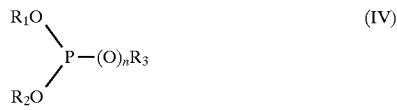

wherein $R_1$, $R_2$ and $R_3$ independently represent $C_{1-4}$alkyl, benzyl or phenyl and n is zero or 1, in a suitable solvent at a temperature within the range 50°–200°. Suitable solvents include hydrocarbons such as n-octane, nonane, toluene xylene, ethylbenzene, halohydrocarbons such as chlorobenzene, dichlorobenzene, dichloromethane, trichloromethane or 1,1,2-trichloroethane, ethers such a tetrahydrofuran, or esters such as ethyl acetate or butyl acetate.

Preferred compounds of formula (III) for use in the cyclisation process include those wherein $R_1$, $R_2$ and $R_3$ are alkyl e.g. ethyl and n is 1 or $R_1$ and $R_2$ are ethyl, n is zero and $R_3$ methyl. Conveniently the latter compounds may be prepared in situ using known procedures.

The hydroxy protecting group R may be removed by well known standard procedures such as those described in Protective Groups in Organic Chemistry pages 46–119, Edited by J F W McOmie (Plenum Press 1973). Thus for example when R is a t-butyldimethylsilyl group this may be removed by reaction with tetrabutylammonium fluoride in acetic acid or by reaction with fluoride ions and a suitable phase transfer catalyst such as tetrabutylammonium bromide in the presence of acetic acid. A particularly suitable source of fluoride ions includes potassium fluoride or cesium fluoride.

The compounds of formula (III) may be prepared from the compound of formula (V)

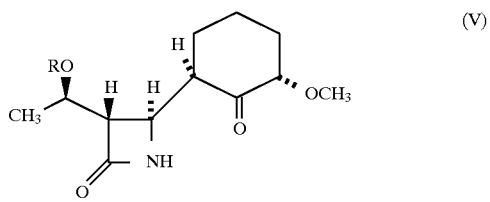

wherein R is as defined in formula (III) by reaction with p-t-butylbenzyloxalychloride in the presence of a suitable base such as, pyridine triethylamine and/or potassium carbonate in solvent such as a hydrocarbon e.g. xylene or cyclohexane, or a halohydrocarbon e.g. chlorobenzene, or dichloromethane or mixtures thereof.

In the above formulae the solid wedge shaped bond indicates that the bond is above the plane of the paper and the broken wedge shaped bond indicates that it is below the plane of the paper.

The following examples are given by way of illustration only:

In the intermediates and examples all temperatures refer to ° C., solutions were dried refers to solutions dried over anhydrous sodium sulphate.

INTERMEDIATE 1

(3S,4R)-1-[4-t-Butylbenzyloxy)oxalyl]-3-(R)-1-(t-butyldimethylsilyloxy)ethyl]-4-[(2'R,6'S)-6'methoxy-1'-oxocyclohexyl]azetidin-2-one To a solution of triethylamine (42.4 ml), potassium carbonate (2.32 g) and 4-[(3S,4R)-3-[(R)-1-(tbutyldimethylsilyloxy)ethyl]-4-[(2'R,6'S)-6'-methoxy-1'-oxocyclohexyl]azetidin-2-one (42 g) in cyclohexane (400 ml), neat p-t-butylbenzyloxalyl chloride (64 g) is added dropwise in ca 10 min. at room temperature under nitrogen. After 10 min., the reaction mixture was washed with water (3×400 ml), and the organic layer was concentrated to ca 125 ml. The obtained solution was diluted with isopropanol (1040 ml) the residual cyclohexane was removed by azeotropic distillation with concentration to approximately 700 ml and then water (230 ml) was added dropwise in ca 10 min. The cloudy mixture was seeded and stirred for 1 hr at room temperature, a further amount of water (450 ml) was then added dropwise in 30 min. and the obtained slurry is stirred for 1 hr at room temperature. The solid was filtered off, washed with a 4/1 mixture water/isopropanol (200 ml) to afford after drying in vacuo at 40°, the title compound (57.3 g) as a white solid (m.p. 68°–69°).

$^1$H-NMR (CDCl$_3$): 7.36 (dd), 5.28 (dd), 4.35–4.25 (m), 3.76 (m), 3.52 (t), 3.33 (t), 3.22 (s), 2.2 (m), 2.1–2.0 (m), 1.68 (m), 1.46 (m), 1.31 (s), 1.19 (d), 0.78 (s), 0.04 (s), –0.05 (s) ppm.

INTERMEDIATE 2

4-t-Butylbenzyl-(4S,8S,9R,10S,12S)-4-methoxy-10[1-(t-butyldimethylsilyloxy)ethyl-11-oxo-1-azatriciclo-[7.2.0.0.$^{3,8}$]undec-2-ene-2-carboxylate.

A solution of intermediate 1 (5.1 g) triethylphosphite (17.8 ml) and hydroquinone (0.1 g) in ethylbenzene (330 ml) was refluxed under nitrogen for 15 hrs, cooled to room temperature and concentrated to approximately 178 ml. The obtained solution was treated with 5% H$_2$O$_2$ (66 ml) and the mixture was stirred for 40 min. The organic layer was washed with 5% aq. Na$_2$SO$_3$ (51 ml), water (51 ml) and then concentrated to an oil which was dissolved in petroleum (153 ml). The obtained solution was washed with water (3–153 ml) and the solvent evaporated to give a clear oil which was dissolved in a 4/1 mixture isopropanol/water (26 ml); azeotropic distillation of the solution afforded the crude title compound. This was dissolved in isopropanol (51 ml) and water (26 ml) was added dropwise over 10 min. The cloudy mixture was seeded, stirred at room temperature for 1 hr and a further amount of water (35 ml) was added dropwise over 15 min. The mixture was stirred at room temperature for 1.5 hrs the white solid was filtered off, washed with a 4/1 mixture water/isopropanol(10 ml) and dried in vacuo at 45° to afford the title compound (4.2 g) as a white solid (m.p. 71°–72°).

$^1$H-NMR (CDCl$_3$): 7.38 (dd), 5.25 (dd), 4.96 (t), 4.2 (m), 4.13 (dd), 3.21 (s), 3.18 (dd), 3.2–3.12 (m), 2.05 (m), 1.9–1.7 (m), 1.7–1.5 (m), 1.5–1.35 (m), 1.32 (s), 1.23 (d), 0.86 (s), 0.8 (s) ppm.

INTERMEDIATE 3

4-t-Butylbenzyloxyoxalylchloride

To a stirred solution of oxalyl dichloride (100ml) in diethylether (500 ml) at –10° under nitrogen a solution of 4-t-butylbenzyl alcohol (200 ml) in diethylether (100 ml) was added dropwise so as to maintain the temperature between –10° and –5°. The solvent was then evaporated under vacuum to give the title compound (289 g,) as a clear oil (b.p. 120°–122° at 2 mbar).

EXAMPLE 1

4-t-Butylbenzyl-(4S,8S,9R,10S,12S)-4-methoxy-10[1-(hydroxy)ethyl-11-oxo-1-azatricyclo-[7.2.0.0.$^{3,8}$]undec-2-ene-2-carboxylate.

Method A

To a solution of intermediate 2 (15.5 g) and acetic acid (9.5 ml) in tetrahydrofuran (53 ml), tetrabutylammonium bromide (40 g) and potassium fluoride (7.3 g, 42–80 mesh) were in turn added. The reaction mixture was then stirred at 50° C. for 4 hrs under nitrogen. After cooling at room temperature the mixture was diluted with ethyl acetate (295 ml) and washed with 10% aq. NaHCO$_3$ (217 ml) and water (2×295 ml). The organic layer was concentrated to 40 ml and slowly added (in ca 5 min), under vigorous stirring, to n-hexane (295 ml). The white slurry was stirred for 1 hr at room temperature and for 1 hr in an ice bath. The solid was filtered off and washed with a 1/1 mixture n-hexane/cyclohexane to afford, after drying in vacuo, the title compound (9.6 g, as a white solid (m.p. 112°–113°).

$^1$H-NMR (CDCl$_3$): 7.4 (dd), 5.35 (d), 5.2 (d), 4.95 (t), 4.25 (m), 4.2 (dd), 3.3–3.25 (dd+m), 3.2 (s), 2.05 (m), 1.9–1.1 (m) ppm.

Method B

Intermediate 2 (2.77 g) was dissolved in tetrahydrofuran (13.6 ml), acetic acid (3 ml) and solid tetrabutylammonium fluoride hydrate (14.3 g) were added in turn and the reaction mixture was stirred at 40° for 3 hrs under nitrogen. The reaction mixture was diluted with ethyl acetate (480 ml), washed with saturated sodium bicarbonate (480 ml), water (2×350 ml) and brine (350 ml). The organic layer was dried and the solvent evaporated to give a clear foam. A 10/1 mixture of petroleum/ethyl ether (70 ml) was added and the mixture stirred at room temperature for 1.5 hrs. The white solid was filtered off and dried under vacuum to give the title compound (1.31 g).

EXAMPLE 2

Sodium (4S, 8S, 9R, 10S, 12R)-4-methoxy-10-(1-hydroxyethyl)-11-oxo-1-azatricyclo-[7.2.0.0.$^{3,8}$]undec-2-ene-2-carboxylate 10% Palladium on carbon (0.42 g) and triethylamine (0.48 ml) were added to a solution of Example 1 (1.22 g) in n-propanol (10.6 ml), under nitrogen. The mixture was hydrogenated for 30 min, the catalyst filtered off washed with acetone (4.2 ml) and solid sodium ethylhexanoate (0.615 g) added to the filtrate solution. Diisopropylether (432 ml) was added dropwise to the solution over 20 min and the mixture was stirred at room temperature for 2 hrs. The white solid was filtered off under nitrogen washed with a 10/2.5/1 mixture of diisopropylether/n-propanol/acetone (2.1 ml) and dried under vacuum to give the title compound (0.38 g) as a white solid.

EXAMPLE 3

Sodium((4S,8S,9R,10S,12R)-4-methoxy)-10(1-hydroxyethyl)-11-oxo-1-azatricyclo[7.2.00$^{3,8}$]undec-2-ene-2-carboxylate 10% palladium on carbon (300 mg) and triethylamine (11 ml) were added to a solution of example 1 (3.2 g) in n-propanol (21 ml), under nitrogen. The mixture was hydrogenated for 45 min at room temperature, the catalyst filtered off, washed with acetone(6 ml) and solid sodium ethylhexanoate (1.34 g) added to the filtrate. Diisopropylether (126 ml) was added dropwise to the solution over 45 min., the mixture seeded and stirred at room temperature for two hours. The white solid was filtered off under nitrogen, washed with diisopropylether(15 ml) and dried under vacuum to give the title compound (1.78 g) as a white solid.

$^1$H-NMR (300 MHZ,) (D2O): 4.74(1H ,m) , 4.08(1H,m), 4.03 (1H dd), 3.28(1H dd), 3.08(3H s), 2.99(1H m), 1.85(1H m), 1.72(1H m), 1.6–1.3 (3H m), 1.20m), 1.11 (3H d)

I claim:

1. In a process for the preparation of a compound of formula (I)

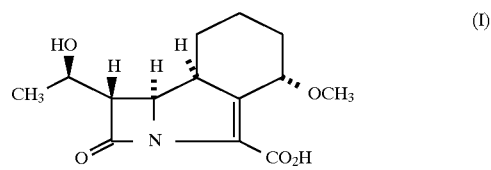

wherein the improvement comprises obtaining a compound of formula (II) in solid form

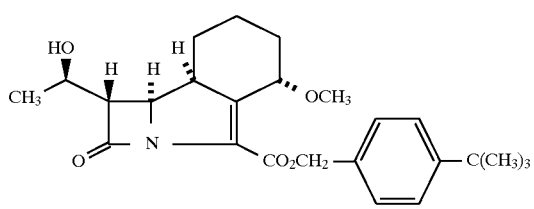 (II)

followed by hydrogenolysis of the compound of formula (II) and optionally converting the thus obtained carboxylic acid into a salt thereof.

2. A process as claimed in claim 1 wherein the hydrogenolysis reaction is carried out using hydrogen and a metal catalyst.

3. A process as claimed in claim 1 wherein the metal catalyst is palladium.

4. A process as claimed in claim 1 wherein the hydrogenolysis reaction is carried out in the presence of a base.

5. A process as claimed in claim 4 wherein the base is a tertiary organic base.

6. A process as claimed in claim 5 wherein the base is a trialkylamine.

7. A process as claimed in claim 1 wherein the compound of formula (I) is isolated in the form of a physiologically acceptable salt thereof.

8. A process as claimed in claim 1 wherein the compound of formula (II) has been prepared by cyclisation of a compound of formula (III):

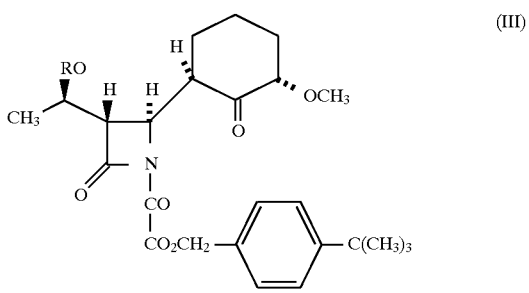 (III)

wherein R is a hydroxyl protecting group followed by removal of the hydroxyl protecting group R.

* * * * *